United States Patent [19]

Gordon et al.

[11] 4,404,972
[45] Sep. 20, 1983

[54] IMPLANTABLE DEVICE WITH MICROPROCESSOR CONTROL

[75] Inventors: Pat L. Gordon, West Columbia; Richard V. Calfee, Houston, both of Tex.; Jay Miner, Sunnyvale, Calif.

[73] Assignee: Intermedics, Inc., Freeport, Tex.

[21] Appl. No.: 264,670

[22] Filed: May 18, 1981

[51] Int. Cl.³ .............................................. A61N 1/36
[52] U.S. Cl. ............................................ 128/419 PG
[58] Field of Search ................................ 128/419 PG

[56] References Cited

U.S. PATENT DOCUMENTS 4,132,233  1/1979  Hartlaub ...................... 128/419 PG
4,164,944  8/1979  Alley et al. .................. 128/419 PG
4,304,237 12/1981  Mensink ....................... 128/419 PG

FOREIGN PATENT DOCUMENTS 2026870  2/1980  United Kingdom ......... 128/419 PG

Primary Examiner—William E. Kamm
Attorney, Agent, or Firm—Hume, Clement, Brinks, Willian & Olds, Ltd.

[57] ABSTRACT

An improved body function assistance device is provided wherein a microprocessor controls the response of the device to various external physiological events and internal timer events. The microprocessor is adapted for use with the limited energy supply available from a battery by activating internal logic components of the processor only in response to selected events and to perform an operating routine corresponding to the "wakeup" event. At the end of the operating routine, a new set of wakeup events is selected and the internal logic components are deactivated. A further reduction in the average operating current is obtained by providing a plurality of counting rates to minimize the number of state changes during counting cycles. The microprocessor may be provided with a fixed operating routine or may be provided with the capability of actually introducing program changes in the implanted device.

24 Claims, 12 Drawing Figures

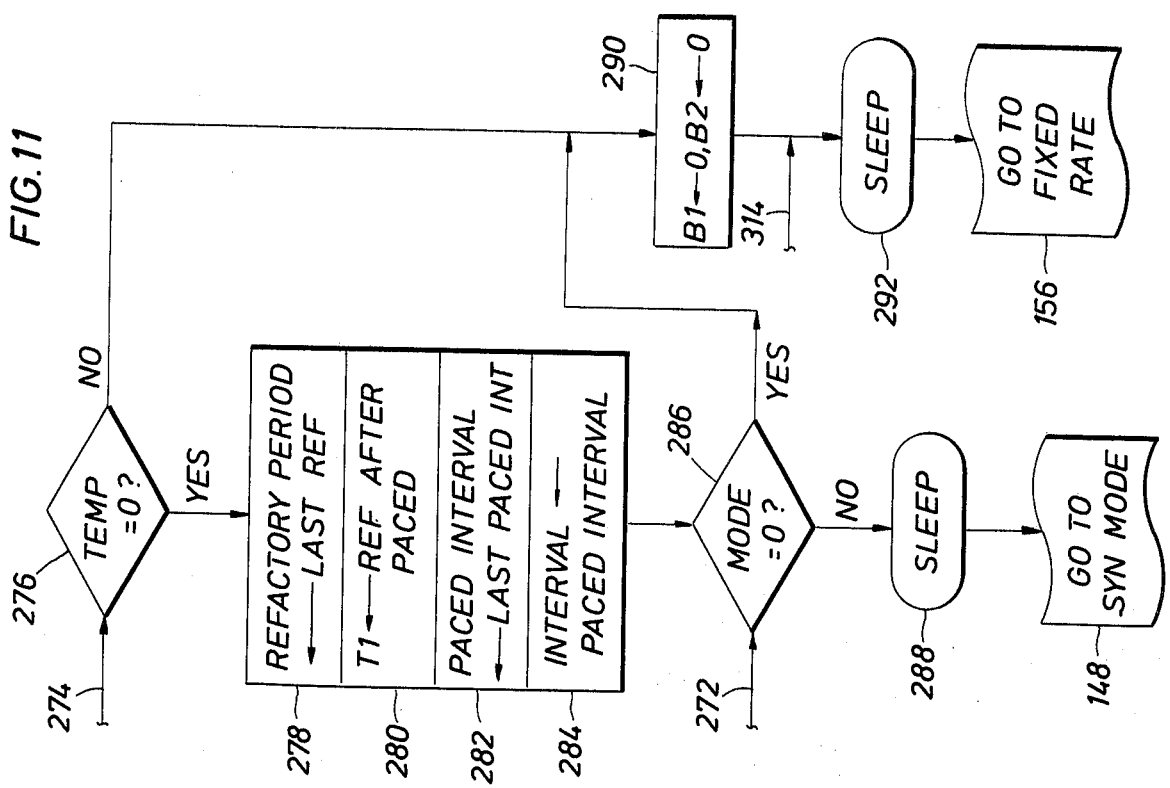
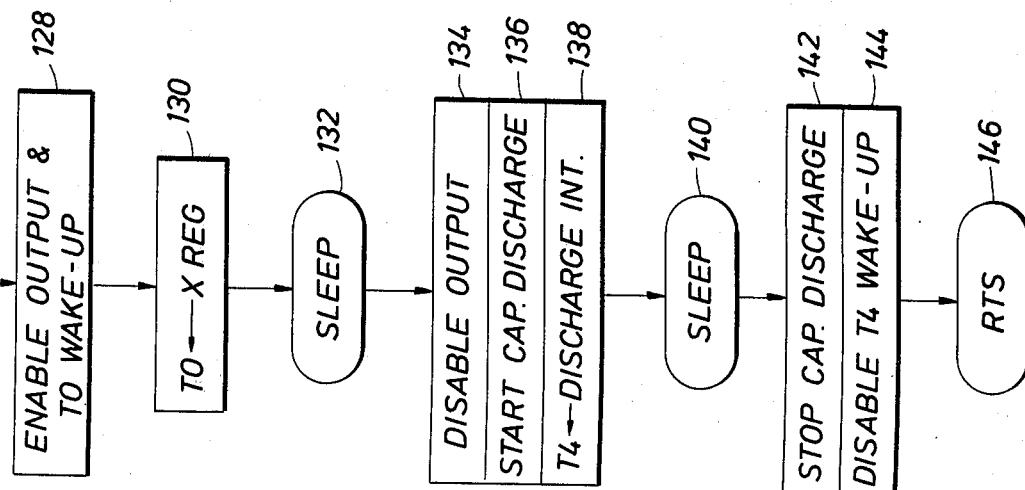
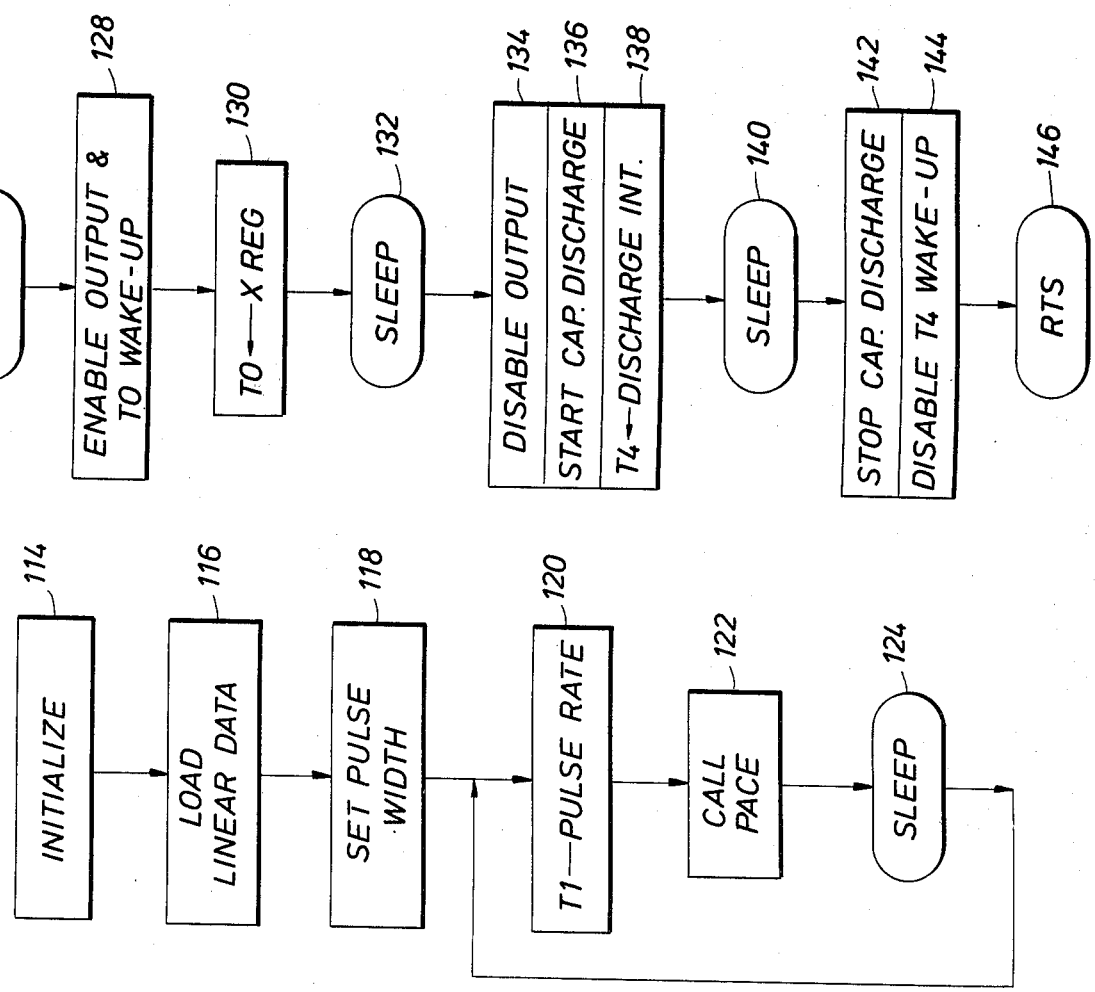

IMPLANTABLE DEVICE WITH MICROPROCESSOR CONTROL

FIELD OF THE INVENTION

This invention relates to implantable body function assistance devices and, more particularly, to implantable devices having controllable output parameters and utilizing microprocessor circuitry for controlling sensing and output functions.

BACKGROUND OF THE INVENTION

A variety of devices exist which may be implanted in a body to supplement or replace natural body functions. Typically, devices may be used to assist the heart in maintaining the steady pumping action needed to sustain life, to control bladder functions, to produce muscle contractions effective to combat scoliosis, to assist in countering pain-producing nerve impulses, and to control the infusion of various solutions into the body. Such devices may be implanted in patients for long periods of time and be required to maintain a selected function over this period of time while powered from a single finite source of energy, typically a lithium battery.

A long lived battery of the lithium type currently available has a total capacity of about 3.2 ampere-hours. Over a typical design lifetime for an implanted stimulating device of seven years, a maximum average current consumption of about 50 microamperes ($\mu$a) can be maintained. Relatively high current consumption can be sustained for short periods of time so long as the average consumption is maintained.

In the developing generation of body function assistance devices, digital electronics are replacing the analog electronics which were originally provided. Using digital techniques, body function assistance devices may be provided which are much more versatile than the analog devices. Digital counters and storage registers combined with improved techniques for communicating information between an external device and an implanted device give such digital devices the capability of varying the output parameters to suit a variety of changing physiological conditions.

In spite of advances in digital electronics, a variety of specialized devices must still be manufactured since each device generally operates only in the sequence built into the device. Changing physiological needs cannot be readily accommodated without changing the implanted apparatus. In addition, the changing physiological needs of a body cannot be analyzed by implanted devices and a response generated which is interactive with the analysis.

The electronics art has developed microprocessors (MP), devices which incorporate the electronic components necessary to perform arithmetic calculations with the small size needed for implantable devices. An MP has the capability of accepting data from various body sensors, analyzing the data, and generating a response appropriate for that particular analysis. Such a device would be suitable for greatly enhancing the capabilities of implanted body function assistance devices. However, such devices have not heretofore been acceptable because of the relatively large power consumption required to operate such devices.

A typical MP using CMOS (complimentary metal oxide semiconductor) technology, having the lowest power consumption presently available, still requires up to 10 milliamperes of current when executing an operating routine. It is readily apparent that such a large current consumption would be unacceptable.

Although some techniques are known in the prior art for reducing the overall current consumption of an MP, such technique, or techniques may not generally be compatible with an implanted body function assistance device. A suitable device must execute instructions reliably and be capable of independent verification of operating instructions in order to be certain that an inadvertent output signal or a loss of output signal does not occur. Further, the device must remain capable of responding to a variety of external physiological conditions in order to maintain its usefulness.

It would also be desirable to obtain the capability of actually changing the operating routine of an implanted body function assistance device. Heretofore, various operating parameters could be changed but not the operating routine itself. However, a typical programmable device requires the use of random access memories (RAM) where the operating instructions must be retrieved from the memory and then returned to the memory, requiring considerably more energy than a read only memory (ROM) where the instructions are fixed in the memory. However, the low power ROM does not afford the capability of altering the operating routine which could be obtained with a RAM.

These, and other problems, have been solved by applicants herein where an improved body function assistance device is provided which utilizes MP technology to monitor and control the operation of the body function assistance device.

SUMMARY OF THE INVENTION

An improved body function assistance device is provided wherein a microprocessor controls the response of the device to various external physiological events and internal timer events. The microprocessor is adapted for use with the limited energy supply available from a battery by activating internal logic components of the processor only in response to selected events and to perform an operating routine corresponding to the "wakeup" event. At the end of the operating routine, a new set of wakeup events is selected and the internal logic components are deactivated.

In a preferred embodiment, an implantable cardiac pacer is provided wherein the average current consumption of the microprocessor is less than 50 microamperes ($\mu$a) and preferably less than 10 $\mu$a and the processor duty cycle is about 10% or less. External events are sensed to derive signals to indicate occurrences such as atrial or ventricular beats, noise, and tachycardiac beats. Internal timers may awake the processor to generate output pulse commands, to sense external events during selected physiological intervals, and to reset various event masks at selected intervals.

The occurrence of a wakeup event initiates a stored operating routine corresponding to the wakeup event. The operating routine stores a next set of wakeup events prior to completing the routine. In the time interval between a completed operating routine and a next wakeup event, the internal logic components of the processor are deactivated and no energy is being expended in performing an operating routine.

A further reduction in the average operating current is obtained by providing a plurality of counting rates to minimize the number of state changes during counting cycles. Thus, intervals which do not require great precision, such as refractory interval, noise interval, or sense interval, may be timed using relatively low counting rates; intervals requiring relatively high precision, such as stimulating pulse width, may be timed using relatively high counting rates.

The microprocessor may be provided with a fixed operating routine or may be provided with the capability of actually introducing program changes in the implanted device. To maintain a low average current consumption, a first operating program may be provided in a ROM. Programmable RAM memory may then be inserted into the ROM sequence using a patch register wherein the occurrence of a program count corresponding to a program count stored in the patch register will cause instructions stored in RAM to be executed and only a relatively small RAM capacity is required.

It is an object of the present invention to control body implantable apparatus generating physiological output signals using a microprocessor.

It is another object to activate internal logic components of the microprocessor only in response to one of a selected set of wakeup conditions.

It is an object for the microprocessor to derive a next set of wakeup conditions functionally related to the previous wakeup occurrence.

It is another object of the present invention to provide an operating sequence for actuating and deactivating the internal logic components of the microprocessor to maintain an average current consumption for the implantable apparatus below 50 $\mu a$.

It is yet another object to provide a microprocessor having a wakeup mask register for storing a selected set of wakeup conditions and for enabling internal logic components of the microprocessor only when a stored wakeup condition occurs.

Still another object is to provide a plurality of timing pulses to provide a desired precision while minimizing the number of pulses generated.

Yet another object is to obtain a reprogrammable operating routine, using RAM for program changes and a patch register for accessing RAM at selected program counts.

SUMMARY OF THE DRAWINGS

FIG. 3 is an interval timing chart following a PACE event.

FIG. 4 is an interval timing chart following a SENSE event.

FIG. 5 is a flow diagram for system initialization after startup or failure detection.

FIG. 6 is a flow diagram for forming an output pulse.

FIG. 11 is a flow diagram for resetting the system following a temporary output condition.

DETAILED DESCRIPTION

As hereinabove described, implantable devices have been provided to assist a number of body functions. The various methods and apparatus hereinbelow described may be utilized in such variety of devices for incorporating an MP into the implantable device to obtain the desired versatility. It is certainly intended that such adaptations fall within the scope of the present invention. However, the following description is specifically directed to the adaptation of an MP for use in an implantable cardiac pacer.

Figure 1:
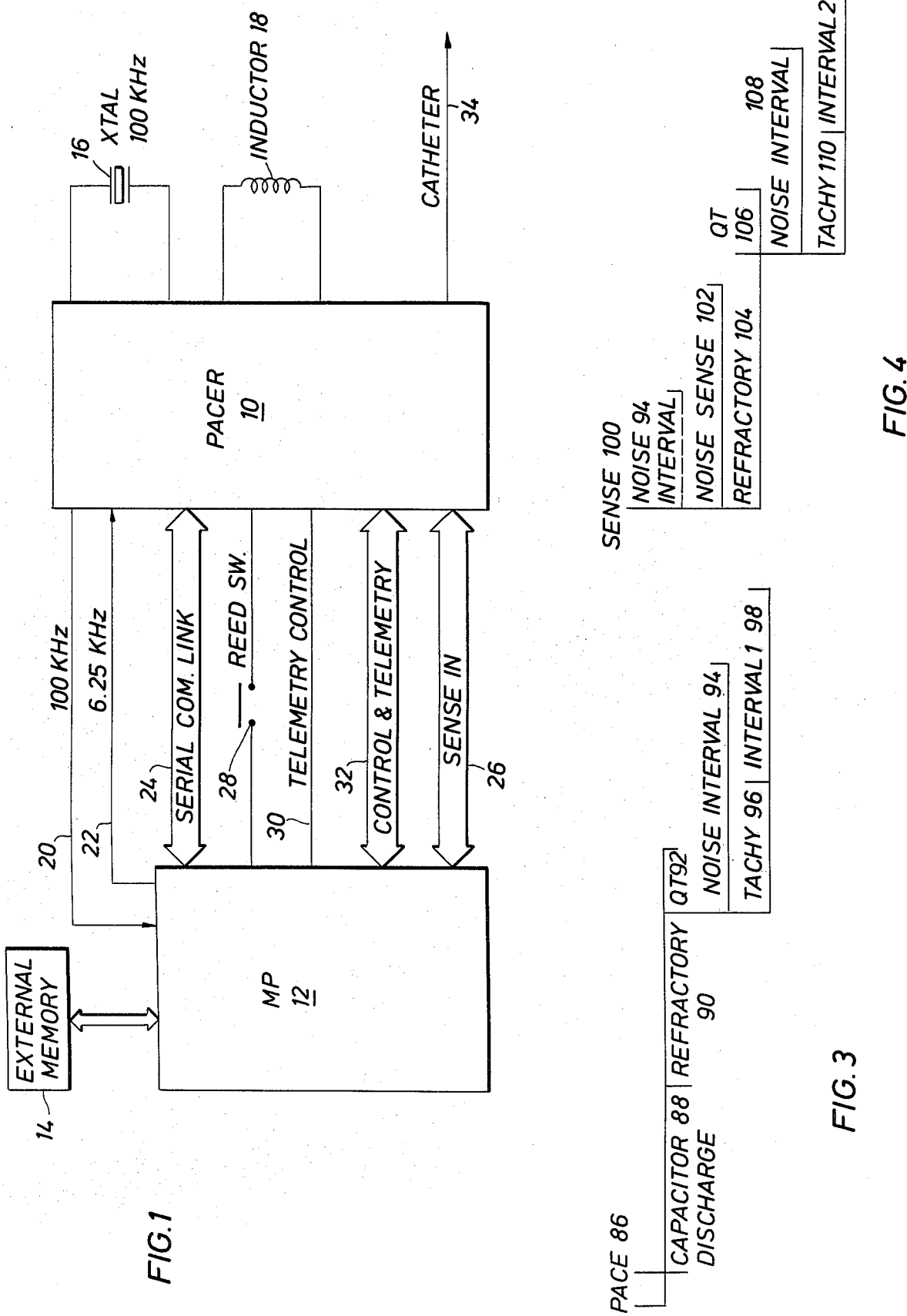
FIG. 1 is a block diagram illustrating basic interconnections between an MP and associated pacer.

Referring now to FIG. 1, there is depicted a block diagram of circuitry comprising an implantable cardiac pacer. Conventional digital technology may be used to provide the actual pacing apparatus 10, such apparatus having output parameters which can be controlled by digital instructions supplied by MP 12 or, in conventional apparatus, by apparatus external to the body and transmitting parameter control signals.

As depicted in FIG. 1, however, MP 12 is contained within the implantable device for controlling pacer 10 circuitry. A single clock circuit 16 may be conveniently used for synchronizing pacer 10 circuitry and MP 12. MP 12 receives inputs 26 from pacer 10 responsive to the occurrence of external events. MP 12 provides pulse control output signals 32 to the pacer for setting the pulse parameter outputs such as pulse width, pulse rate, or pulse amplitude. Further, data may be serially transferred 24 between pacer 10 and MP 12 for telemetric communication with external apparatus. If desired, MP 12 may be provided with additional memory capability 14 external to MP chip 12 for use in expanded programming or data processing.

In a preferred embodiment, basic timing pulses are generated at 100 KHz by clock 16 and transferred 20 to MP 12. MP 12 may then conveniently generate synchronized pulses at lower frequencies which can be transferred 22 to pacer 10 for selected functions.

Generally, data input and telemetry output may be through coil 18, or through different coils. Reed switch 28 is conventionally included for activating during telemetry events. Switch 28 provides a positive signal for system use. Telemetry control 30 likewise provides control signals for data transfer.

During operation, MP 12 accepts sensed input 26 for analysis during selected wakeup intervals, as hereinafter discussed, and provides control signals 32 to pacer 10 responsive to the wakeup event which has been detected and analyzed. After a telemetry transfer, pacer 10 must be serially provided 24 with operating parameters to replenish the register information which has been serially transmitted. Pacer 10 produces an output pulse on catheter 34 corresponding to the stored pulse parameters.

Figure 2:
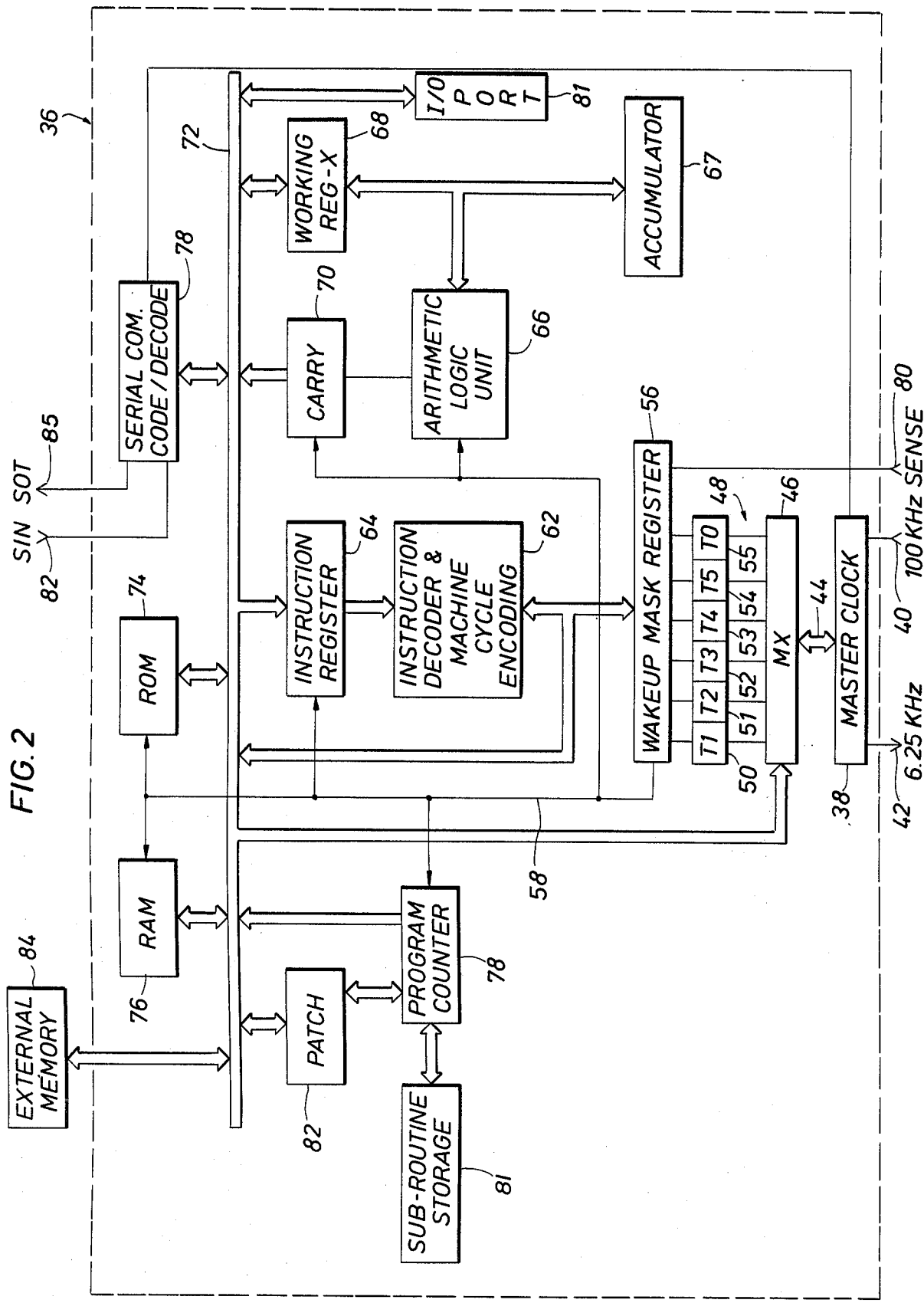
FIG. 2 is a block diagram of MP architecture.

Referring now to FIG. 2, there is shown a block diagram of component parts of a microprocessor 36 having features hereinbelow described. The internal logic components of MP 36 execute a stored program routine for analyzing various sensed input data and performing logical operations as required by the operating routine. Thus, the operating routine is generally stored in memory 74, which may be ROM. The desired operation is selected by a program counter 78 and transferred to the instruction register 64 along the internal data bus 72. The instruction is further decoded 62 and processed to derive command signals for the arithmetic logic unit (ALU) 66 and for moving data to and from the working register 68 and various internal registers and external ROM and/or RAM memories 84. ALU 66 performs the manipulation indicated by the program and by the presence of any flags as determined by decoder 62. As hereinafter discussed, a patch register 82 may also be used to control ALU 66. Data and instructions may be transferred in and out of MP 36 to various buffer ports 80, 82, and 84 or through a conventional input/output (I/O) port 81.

The above description generally relates to any MP architecture and may be implemented in any number of circuit configurations, which architecture is not the subject of the present patent application. The features herein discussed relate to the wakeup features afforded by wakeup mask register 56 and reprogramming features afforded by patch register 82. These features are particularly discussed herein.

In conventional MP operations, the program routine operates to generally step through the program sequence as determined by a timing and control circuit in a program counter. Thus, a conventional MP is continuously testing for the presence of flags and performing data analysis. Such a closed loop operation would not be acceptable for an implanted MP because of the large current consumption required to continuously cycle the program.

In order to provide an MP suitable for implantation, it is necessary to reduce this current consumption. A major reduction may be accomplished by activating, or waking up, MP 36 as infrequently as possible, processing the information as determined by the wakeup event, setting MP 36 for another wakeup event, and thereafter executing a sleep request to deactivate MP 36. In this regard, a first instruction acts to set MP 36 and wakeup mask 56 to a set of wakeup conditions which has been determined by the previous wakeup event and by the condition analysis performed by MP 36 and a second instruction causes MP 36 to go to a sleep state. To the maximum extent possible, the internal logic components are, in effect, disconnected from the timing and control circuits and none of the internal logic component states are changed during the sleep state.

As herein contemplated, an instruction just prior to the sleep request provides an instruction set to wakeup mask register 56 corresponding to a selected set of wakeup conditions. Typically, MP 36 may wakeup to test for the end of the heart refractory period, in response to a detected ventricle and/or atrial beat, to compute output pulse parameters, to analyze sensed inputs for noise, and to reset wakeup timers at selected intervals. In the context of a cardiac pacer, it is possible to obtain a duty cycle, the ratio between internal logic component on-time in a selected interval to the whole interval, to less than about ten percent. A preferred operating sequence achieving this duty cycle is hereinafter explained with reference to FIGS. 5-12.

As depicted in FIG. 2, wakeup mask register 56 is loaded with a coded signal corresponding to the desired set of wakeup events. Wakeup mask register 56 is also supplied with inputs from various timers 50-55, which may be internal to MP 36, and from sense amplifier output 80 in the pacer circuitry. A true flag from a timer 50-55 or a sense amplifier output 80 corresponding to a data bit in the wakeup mask register 56 produces a timing output which enables the internal logic circuits to respond to clock pulses and continue an operating sequence corresponding to the actual wakeup condition.

A variety of counters 50-55 are provided to correspond to selected intervals relating to heart physiological characteristics. A timer 50-55 is conveniently set by being loaded with a count complementary to the desired count wherein the counter is incremented to produce a carry bit on rollover for timeout. Of course, the counter could be loaded with the desired count and count down to zero, if desired. The desired timeout intervals are provided by operation of MP 36 and timers 50-55 are loaded just prior to a sleep period.

In order to further conserve energy, timers 50-55 may be clocked at different pulse rates. The desired timeout intervals cover a variety of actual time periods and the various intervals have a variety of precision requirements. Thus, in a preferred embodiment, count intervals of 0.01 ms to 81.92 ms are provided to obtain timeout periods of 2.56 ms to 20.97 sec. A master clock divider circuit 38 is provided for obtaining the desired clock pulse rates from a single master clock input 40. Table A sets forth the preferred correlation between the control information and available clock frequencies from divider 38.

TABLE A

| TIMER | CLOCK FREQUENCIES AVAILABLE (KHz) | FUNCTION |
|---|---|---|
| T0 | 100, 50, 25, 12.5 | Output pulse generation |
| T1 | .0977, .0488, .0244, .0122 | Noise sense interval, refractory period, tachycardia interval, pace or sense interval, |
| T2 | | QT interval, |
| T3 | 1.56, .78, .39, .195 | Noise interval, Capacitor discharge, |
| T4 | | Triggered mode |
| T5 | | rate limit |

It should be noted at this point that a CMOS MP retains a given state condition and energy is required only to change from one state to another. Energy is thus conserved by minimizing the number of pulses required for the various timeouts. Of course, the same total number of program steps are required to complete a given operating routine in MP 36, so a frequency change has little effect on the energy consumed by the internal logic circuitry of MP 36, but a large effect on the energy consumed by the timing circuitry 50-55 of MP 36 and the external components.

Another energy saving routine may also be incorporated in the internal logic circuitry. A conventional program counter may frequently execute address instructions in a binary sequence. It may be shown that a counter of infinite length operating to produce a straight binary count will have two state changes for each unit incremental change. If a different operating sequence is used, it is possible to reduce the number of state changes for each unit incremental change to a single state change. This may be done by executing instructions according to a grey code where, by definition, only a single state change is required for a single unit incremental change.

A typical address register is not of infinite length, which precludes realizing the full savings with respect to the number of state changes. Nevertheless, grey code operation is believed to be yet another technique for adapting an MP to an implantable pacer.

As depicted in FIG. 2, six timers 50-55 are provided to correspond to various physiological events and pacer events. Timer 50, T1, may be an overall interval timer and, as shown in Table A, has the capability of counting for long periods of time in relatively coarse increments. Another timer 51, T2, may be provided to adjust the total refractory interval, i.e. the interval within which a stimulating pulse will not produce a corresponding heart response, to obtain a stored time within which no signal would be expected. Still another timer 52, T3, may be provided to monitor sense events over a selected interval and permit MP 36 to determine whether a sensed event comprised a heartbeat or noise. Timer 53, T4 may be provided to activate a switch in the pacer circuit for improved capacitor discharge in the pacer 10 circuit. Timer 54, T5, may be provided to obtain a rate limiting function when the pacer circuit is operating in a synchronous mode.

Finally, timer 55, T0, may be provided to time the duration of an output pulse. The duration of an output pulse is preferably short and the control precision desired is relatively high. Accordingly, T0 may be operated up to the highest available clock frequency, which is preferably 100 KHz for obtaining incremental changes as small as 0.01 ms.

In addition to timed wakeup events, various sensed event inputs 80 may also wakeup MP 36. Thus, specific event wakeup masks may be provided in association with MP 36 timed wakeup masks to enable sensed wakeup events to wake up MP 36. Sensed event inputs 80 may include an atrial beat and/or a ventricular beat. The sensed event masks are enabled to wakeup MP 36 where the appropriate bit in the wakeup mask register 56 was set during the previous sleep request.

MP 36, as hereinabove described, has the capability of executing any operating routine stored in the program memory associated with MP 36. Program steps may be stored in either ROM 74 or RAM 76. However, executing a program from RAM 76 may require that the program instruction be fetched from RAM 76 and then returned to a location within RAM 76. Executing an instruction from ROM 74 requires only that the instruction be transferred to a working register, e.g., register 68. ROM retains the instruction without further action by the program. Further, commercial RAM units typically have more components than ROM, wherein a given state change requires more power in a RAM unit than a ROM unit. Thus, it is apparent that executing an instruction from RAM 76 requires more energy than executing an instruction from ROM 74.

It is also apparent, however, that ROM 74 instructions cannot be changed. Further, once an implantable device has been implanted it is not accessible for ROM substitution. Thus, while providing an implantable body function stimulating device with MP 36 greatly increases the capabilities of the device to respond to a variety of changing physiological conditions, such a device utilizing ROM only must continue to operate with a fixed operating routine.

Several pacer designs currently exist which have the capability of providing alterable pacer output pulses. Various pulse parameters such as rate, width, and amplitude can be changed from time to time through application of external signals. However, only the parameters can be changed by external equipment. Such devices have been labeled as programmable pacers when, in fact, actual programming in the sense of altering the operating routine is not possible.

As hereinabove shown in FIG. 2, patch register 82 in MP 36 and RAM memory 76 and 84 is provided which may be either external or internal to MP 36. Patch register 82 uniquely provides reprogramming capability for the implantable body function stimulator, as hereinafter set forth. An actual change in the operating routine of the implanted device can now be effected to compensate for changing physiological needs without having to explant the device.

In basic operation, a program change may be communicated to MP 36 by radio frequency communication, or by any other method known in the art, but preferably using the method and apparatus set out in U.S. patent application Ser. No. 972,231 to Calfee, et al., assigned to the same assignee as the present application, which disclosure is incorporated herein by reference, wherein a verified digital signal can be transmitted from an external device to an implanted internal device. This signal may awake MP 36 for reprogramming through the serial ports 82 and 85 and register 78. Patch register 82 may be loaded with a programming count number corresponding to a portion of the operating routine which is to be altered. The altered operating routine is then stored in a RAM 76 or 84 address. When program counter 78 reaches a count corresponding to the count in patch register 82, the operating routine first proceeds to an initial address in RAM 76 which, in turn, contains the address of the stored routine which is to be executed. The new instructions in RAM 76 or 84 are executed until the operating routine is complete. Generally, the last operating routine in RAM 76 or 84 will return the control to another location in ROM 74.

RAM 76 or 84 instructions may be effective to interrupt the ROM 74 program at several program counts. Thus, the final operation in a RAM 76 or 84 sequence may be to load patch register 82 with the next program count where RAM 76 or 84 operating routine is to be substituted for ROM 74 routine. The reprogramming capability afforded in the device will be determined by the battery capability to support RAM 76 and 84 programming and the corresponding bit spaces reserved for RAM 76 and 84.

Where RAM 76 and 84 is provided, the preferred embodiment includes operating instructions which verify at least one characteristic of the instruction byte. In a preferred embodiment, the desired characteristic to verify is the parity of the instruction. If an error is introduced, it is most likely that only a single bit will be affected and that a parity check will reveal the error. The programming may be accomplished where every instruction byte has an even number of bits. Then, bit 7 of the first byte of every instruction may be reserved as a parity bit to force the total number of true bits to an even number. If a parity check reveals an instruction error, the program counter moves to the fixed rate pacing program and remains there until the memory contents can be interrogated and the error corrected.

Referring now to FIGS. 3 and 4, there are depicted in timed relationship the various timed events which occur following a selected cardiac event. FIG. 3 particularly relates to the timed wakeup events which occur following the delivery event of a cardiac pulse by the pacer. FIG. 4 depicts the series of timed events which occur after an external event has been sensed, which may or may not be a naturally occurring cardiac pulse. As hereinabove set forth, the microprocessor is only activated upon the occurrence of selected events, either timed intervals or external events, and sleeps between such events in order to maintain power usage within acceptable average limits.

Referring now to FIG. 3, there is depicted a series of timed events which occur following the delivery of a stimulating pulse by pacer circuitry 10 (see FIG. 1). Following the delivery of a pulse to the output lead, there is an interval for discharging the capacitor created by the patient's body and the implanted electrode lead. After capacitor discharge interval 88 is completed, refractory interval 90 is loaded into a timer. The refractory period of a heart is the period during which the various stimulated nerves are depolarized and incapable of responding to a stimulating pulse. The timed refractory interval 90 is adjustable to accommodate the actual expected physiological response of the patient.

Following the refractory period 90, the timers are then loaded with a variety of timed intervals. A quiet time interval "QT" 92 is provided for obtaining an indication that a selected period of time has elapsed within which no cardiac event is sensed. In parallel with QT period 92, noise interval 94 and tachycardia detection interval 96 are established, as hereinafter explained.

Thus, during QT interval 92, three timers are activated to awaken the processor at selected times. During the intervals, cardiac events are being sensed and latches set for use in determining whether the indicated condition, i.e., noise, tachycardia, or cardiac beat, has occurred. If a cardiac event occurs during QT interval 92, the QT timer is reset to begin another QT interval 92. Thus, QT interval 92 may continue to reset unless about 41 ms. elapses without detecting any input signal. This period effectively resets the beginning of the final QT interval 92 until the end of a "T" wave following the paced event. In this manner, a variable refractory period is obtained adapted to locate the "T" wave under changing physiological conditions.

Tachycardia interval 96 then times out and the processor examines the various detected events, as hereinafter discussed, to determine whether a tachycardia has occurred. The occurrence of a tachycardia can simply be stored at a selected memory location for subsequent interrogation or might initiate a tachycardia arrest routine, if provided. At the end of tachycardia interval 96, a sense interval INTERVAL I 98 is loaded into the timer for the final timing sequence, within which a spontaneous ventricular beat is detected or at the end of which another pacer pulse 86 is generated.

In parallel with tachycardia detection interval 96 and at least a portion of INTERVAL I 98, noise interval 94 is provided for collecting information for evaluation of sensed events. The various events sensed by the pacer system may be an actual cardiac waveform or may be noise introduced into the system from external electrical signals or other body generated electrical signals. The incoming signals are, thus, evaluated so that only a selected waveform can activate the pacer operating routine corresponding to a spontaneous ventricular contraction. If the stored data is processed and a noise determination is made, a paced event 86 occurs at the end of noise interval 94.

Referring now to FIG. 4, there is depicted the various timed conditions which occur once a sense event 100 occurs. As hereinabove stated, sense event 100 may be an actual spontaneous ventricular contraction, or may be noise. Thus, sense event 100 may occur during noise interval 94 and, if so, noise interval 94 simply continues until timeout. Sense event 100 then causes timed events for another noise sense interval 102 and a new refractory period 104 to begin. Noise sense interval 102 accumulates additional sensed events. At the end of noise sense interval 102, the number of events is then examined for a noise determination. The duration of noise sense interval 102 and the number of events defined to identify noise are both variable parameters herein.

Refractory interval 104 is generally the same as refractory interval 90, hereinabove discussed, and is followed by QT interval 106 and corresponding noise interval 108 and tachycardia detection interval 110. These intervals all operate substantially as discussed hereinabove for FIG. 3.

Following timeout of tachycardia detection interval 110, the particular timer is reloaded with INTERVAL II 112. It should be noted here that INTERVAL II 112 is not identical with INTERVAL I 98 since the system priority is biased in favor of spontaneous ventricular contractions. Once a spontaneous contraction has occurred, the system is substantially reset to expect another spontaneous contraction. Hence, INTERVAL II 112 is longer than INTERVAL I 98. In a preferred embodiment, INTERVAL II 112 is set to about 60 beats per minute, a rate sufficient to sustain activity but which permits a full period within which a spontaneous ventricular contraction should occur, if it is going to occur. If a spontaneous ventricular contraction does not occur, i.e., a subsequent sensed event 100 does not occur, then a paced event 86 occurs and the sequence of FIG. 3 is again carried out including INTERVAL I 98.

As hereinabove set forth, the apparatus providing the timing inputs and processing capability is preferably a microprocessor contained in a single "chip" and having the architecture set out in the description of FIG. 1. The microprocessor then processes the various input events to determine the appropriate timing conditions to load into the system timers and to initiate a pacer output pulse when approproate. A description of this operation is hereinbelow set forth with reference to various program flow diagrams. It should be recognized that these flow diagrams may be implemented by a variety of computer language program listings which may be readily prepared by persons of ordinary skill in the computer art. The following flow diagrams, however, embody the features of the present invention which relate to cardiac pacers and which obtain the features which provide a fully functional implantable cardiac pacer having the capabilities hereinabove described.

Referring now to FIG. 5, there is depicted the program routine for initializing the programmable pacer when the pacer is activated for the first time or after a parity error is discovered, as hereinafter described. The operating parameters are first initialized 114 in selected storage locations of the processor and the processor is instructed to load 116 the linear operating parameters into pacer circuitry 10 (see FIG. 1). The pulse width is set 118 and T1 is loaded 120 with the pulse rate. When T1 times out, a sub-routine PACE (see FIG. 6) is called 122, after which the processor sleeps 124 while T1 is again timing out. Thus, a simple fixed rate pacing routine is first established.

As hereinafter described, a sub-routine is provided for performing a paced event, as depicted in FIG. 6. Thus, PACE sub-routine 126 is called by the main program to initiate an output pulse. The processor enables the pulse output gate in the pacer circuitry 10 (see FIG. 1), sets the wakeup mask to correspond to the contents of timer T0 at 128, loads 130 the contents of operating register X into T0 which initiates generation of an output pulse. The processor then returns to a sleep condition 132. As T0 times out, output pulse gate in pacer 10 (see FIG. 1) is disabled 134 and the processor is then awaked to activate 136 an electronic switch to discharge capacitive elements charged during the pulse output, and to load 138 the capacitor discharge interval into timer T4. The processor thereafter returns to sleep 140. As timer T4 times out, capacitor discharge is stopped 142 and the T4 wakeup mask is disabled 144. Control of the processor is then returned 146 to the main operating routine.

Figure 7:
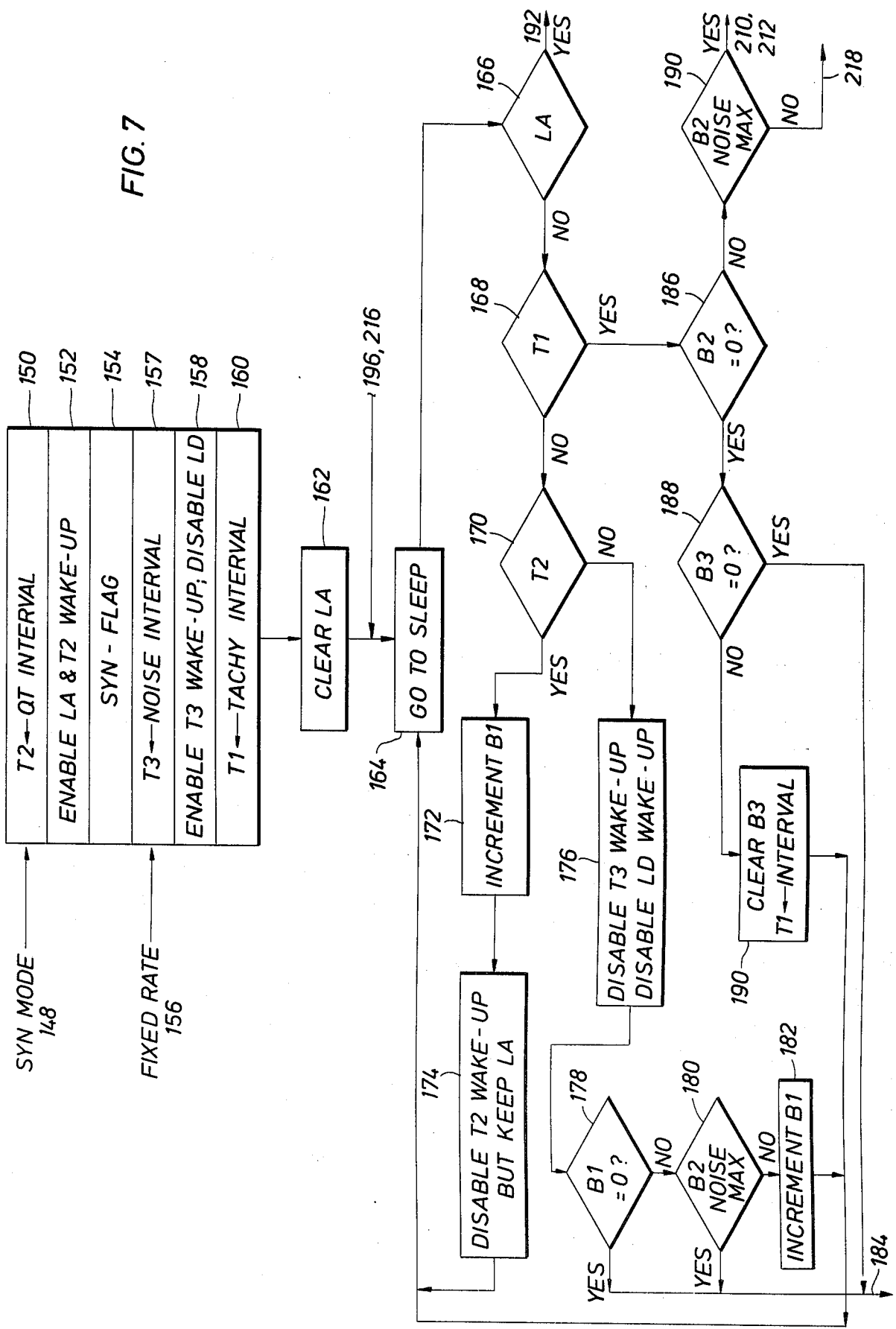
FIG. 7 is a flow diagram for wakeup event determination.

FIGS. 7 through 12 depict a preferred operating routine implementing the various intervals depicted in FIGS. 3 and 4. Referring now to FIG. 7, it is convenient to begin the description of the operating routine beginning at the end of a refractory period timeout. The pacer may be either in a synchronous mode 148 or a fixed rate 156 mode of pacing.

Where a synchronous mode of operation is selected, the processor awakens at the end of the refractory period and the QT interval is loaded 150 into timer T2. The wakeup mask is enabled 152 for both T2 timeout or the occurrence of a sensed ventricular input at latch LA. A system flag is set 154 to indicate selection of the synchronous operating mode. Simultaneously, noise interval timer T3 is set 157 and the appropriate wakeup mask is set 158 for T3. As set out in FIG. 7, another latch LD is disabled during step 158 for purposes of program compatibility.

Further, tachycardia interval timer T1 is loaded 160. The tachycardia detection interval can be varied. In this regard, the tachycardia detection mode can be effectively circumvented, if desired, by setting the interval to a time less than the QT interval. Finally, the processor clears 162 any input signal which may be present at wakeup latch LA and goes to sleep 164 with the wakeup conditions now established.

It should be noted that a fixed rate pacing mode 156 is initiated by entering the operating routine at step 157. Timer T2 and latch LA wakeup registers are not enabled for a fixed rate pacing mode since, by definition, a pulse will be delivered at a fixed interval following a first pulse.

When the processor receives an input signal indicative of a wakeup event, the wakeup register is interrogated to determine the nature of the wakeup condition. Latch LA is interrogated 166 for a sense event. In the absence of a sense event, timer T1 is interrogated 168 for the end of the tachycardia interval. If timer T1 has not timed out, then timer T2 is interrogated 170 for the end of the noise detection interval. If T2 has timed out, then the QT interval is over and a flag B1 is incremented 172 to indicate this event. The processor disables 174 the T2 wakeup but maintains a sensed event wakeup condition through latch LA. The processor returns to sleep 164.

When the next wakeup event occurs, the processor again interrogates latch LA 166, timer T1 168, and timer T2 170. If T2 is not in a timeout condition, then only T3, the noise interval timer, remains and the processor hereafter disables 176 the wakeup condition from timer T3 and latch LD. The processor now determines whether the presence of noise is indicated or whether T3 has timed out without the QT interval timing out. Thus, flag B1 is interrogated 178. If B1 is "0," this is indicative of the noise interval being completed prior to QT interval timeout, a condition the system interprets as a noise condition and proceeds 184 to a pace condition (see FIG. 10). If B1 is not "0," then the QT interval is over and the noise interval is over, and the processor interrogates 180 B2, a sensed event counter. If B2 has been incremented the number of counts necessary for a noise condition, the processor also signals 184 for a paced event (see FIG. 10). If a noise condition is not indicated, then B1 is incremented 182. Thus, if B1 is now equal to "2," both the QT interval and the noise interval are over. The processor returns to sleep 164.

At the next wakeup event, the processor agains interrogates sense latch LA 166, and timer T1 168, the tachycardia interval timer. Now, if timer T1 has timed out, the processor determines whether a tachycardia has occurred. Counter B2 is interrogated, which has collected sensed events as hereinafter described. If B2 indicates the presence of sensed events, the contents are compared 190 with the noise condition. If a noise condition is indicated, the signal is processed further 210, 212 to determine whether a pacing sequence should be initiated (see FIG. 8). If counter B2 does not indicate noise, but nevertheless indicates that sense events were detected during the tachycardia interval, then the tachycardia analysis sequence is activated 218 (see FIG. 9).

If B2 is "0," i.e., no sensed events have yet occurred, then B3 is interrogated 188 to determine whether the T1 timeout indicates a tachycardia interval timeout or a paced interval timeout. If B3 is not "0," then the tachycardia interval has timed out, B3 is reset 190 to "0," and the appropriate interval from the interval register is loaded 190 into T1, and the pacer goes to sleep. The interval loaded 190 into T1 is either the paced interval or the sensed interval which has been loaded into the interval register following event determination, as hereinafter described. Thus, during the next sequence, B3 will now be "0," in the absence of any intervening sensed events, indicating that the entire sensed period has now expired without sensing any suitable cardiac input and a pacing sequence is initiated 184 (see FIG. 10).

Figure 8:
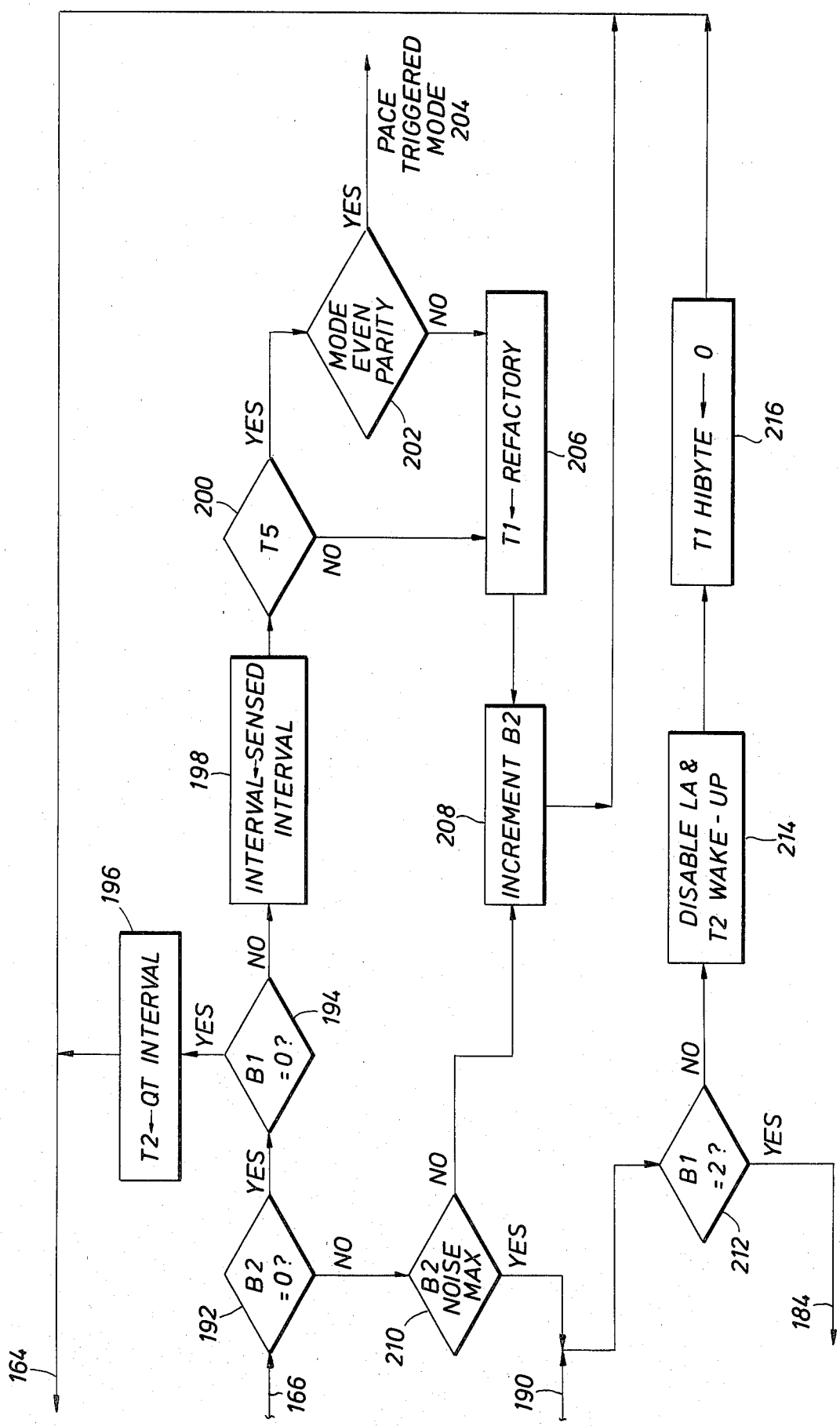
FIG. 8 is a flow diagram for noise detection.

Finally, if the interrogation 166 of latch LA indicates that a sensed event has occurred, then the sequence depicted in FIG. 8 is initiated. Counter B2, the sensed event counter, is interrogated 192. If B2 is "0," then the sensed event must be examined to determine the nature of the event. Counter B1 is interrogated 194 to determine whether the QT interval has expired. If B1 is "0," the QT interval has not yet expired and timer T2 is reloaded 196 with the full QT interval. Thus, the occurrence of a sensed event in the QT interval does not increment the noise counter but does reset timer T2. This continues until timer T2 timeout, whereupon B1 is incremented. After the end of the QT interval, thus, the first sensed event loads 198 the interval register with the count for the interval period which follows a sensed event.

In the synchronous mode operation, the ventricular beat may be used to inhibit a pulse production from the pacer or may be used to synchronize production of a pulse, the "pace triggered mode." If the triggered mode has been selected, timer T5 will control production of the pulse following the ventricular beat and timer T5 is interrogated for timeout. If T5 is not in a timeout condition, the refractory period is loaded 206 into timer T1 and event register B2 is incremented 208. If timer T5 is timed out, the operating mode is interrogated 202. If a mode check determines the presence of even parity, the pace triggered mode is selected to activate the pacer output (see FIG. 10).

If there is no indication of the triggered mode, the refractory interval is loaded 206 into timer T1, B2 is incremented, and the pacer again goes to sleep 164. On the occurrence of a next sensed event 166 (FIG. 7), B2 is no longer "0" and the noise comparison is interrogated 210. If the maximum noise count is not reached 210, B2 is again incremented 208 and the processor returns to sleep 164.

Once the noise maximum has been reached 210, counter B1 is interrogated 212 to determine whether the noise interval is over. If the noise interval has been completed, then a pulse generation sequence is initiated 184 (see FIG. 10). If the noise interval is not yet over and the counter is already full, the operating sequence then disables 214 any further wakeup from sensed input conditions at latch LA and QT interval timeout since a pulse will now automatically be generated at the end of noise interval timeout T3. In this condition, the tachycardia interval timer T1 is loaded 216 to a condition effective to extend the timeout beyond the timeout of noise interval timer T3. The only remaining wakeup condition is noise interval timer wakeup and a pacing sequence will be initiated upon the occurrence of that condition. Thus, the presence of noise detected by the system will cause a pulse to be generated as a safety measure.

Figure 9:
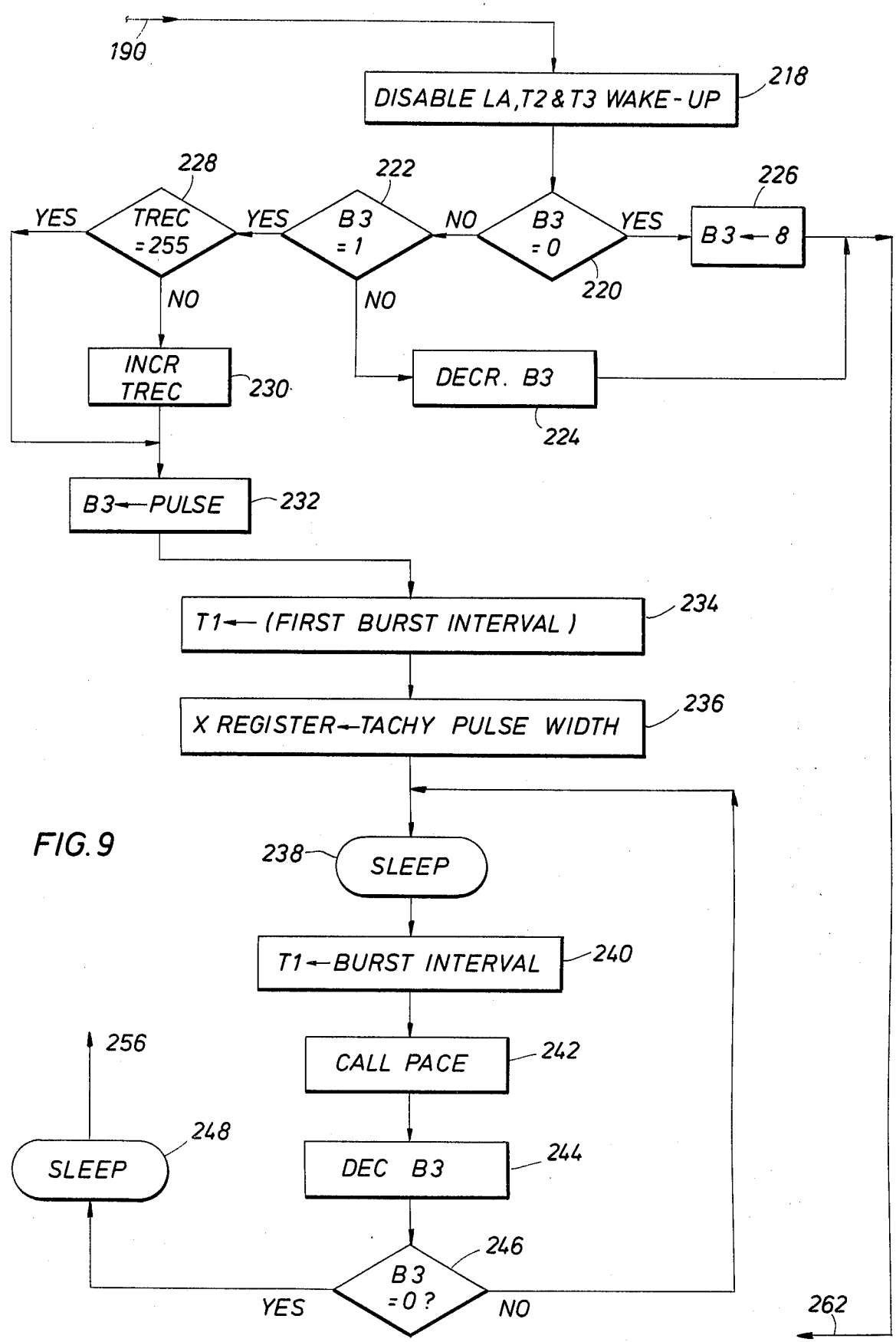
FIG. 9 is a flow diagram for tachycardia detection and treatment.

Referring now to FIG. 9, there is depicted a tachycardia analysis and correction routine. When the tachycardia interval timer T1 times out 168 (FIG. 7) and the noise counter B2 is not "0" 186 (FIG. 7) and the noise comparison 190 is not affirmative, then the operating sequence assumes the sensed events were tachycardiac and initiates the operating routine shown in FIG. 9. The processor first disables 218 the wakeup corresponding to a sensed event at latch LA, timer T2, and timer T3. Counter B3 is then interrogated 220 to determine whether the selected number of tachycardiac beats has occurred which is sufficient to require a correcting routine. On the first tachycardiac beat, B3 is "0" and the routine loads 226 B3 with a selected count, which may be "8." The processor then proceeds 262 through the routine as if a normal ventricular beat had been sensed. As hereinafter discussed, B3 may have already been set to an "8" count and will not be "0" at interrogation 220. Counter B3 is then interrogated 222 to determine whether a "1" count exists. If not, the counter is decremented 224, and again the sensed event is treated as a normal ventricular beat. However, when sufficient tachycardiac events have occurred to decrement counter B3 to a count of "1," a tachycardia routine may be initiated.

It is desirable to record the number of actual tachycardia conditions derived by the system and a tachycardia recording counter is interrogated 228 which can count up to 255 events. If the counter is not full, the contents are incremented 230. If the counter is full, the incrementing step is by-passed and counter B3 is loaded 232 with a selected number of pulses to be generated by the pacer in response to the tachycardia. Timer T1 is then loaded 234 with a selected interval after which the first pulse is to be generated. Finally, the X register is loaded 236 with the width of the tachycardiac pulses to be generated.

The processor then goes to sleep 238. Upon wakeup at T1 timeout, the processor simultaneously loads 240 timer T1 with the time between successive pulses and calls PACE subroutine (see FIG. 6). After each pulse is generated, counter B3 is decremented 244 and the contents interrogated 246. Thus, the pulses in the burst continue to be generated until counter B3 is decremented to "0," whereafter the processor goes to sleep 248 and returns to a normal pace routine (see FIG. 10). A single burst of pulses is generated by the sequence depicted in FIG. 9 and the tachycardia system is reset, as hereinafter set forth, until a subsequent determination is made that the tachycardia is persisting.

Figure 10:
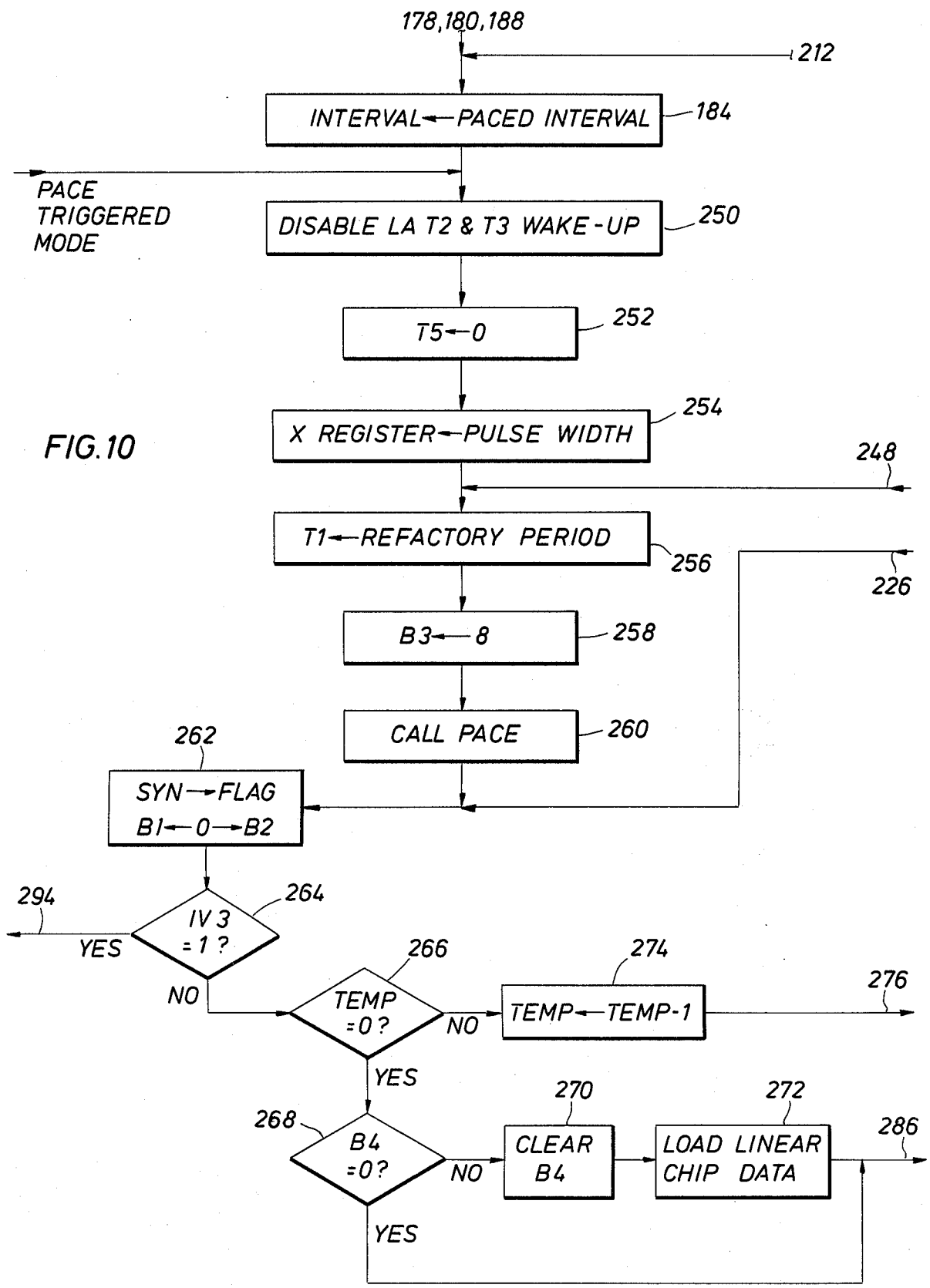
FIG. 10 is a flow diagram for generating an output pulse having selectable parameters.

Referring now to FIG. 10, there is depicted the operating sequence which occurs once a determination is made that a pacer pulse is needed. As hereinabove noted, these conditions include a determination that the paced interval has expired without sensing a spontaneous ventricular beat, a determination that the noise interval has expired while the QT interval continues to reset itself, a condition that noise is detected, a triggered response to a previous spontaneous ventricular beat, a normal pulse following a tachycardiac burst, and a pulse following a determination of tachycardia.

Where the enabling events are a noise interval timeout, or a ventricular sensing interval timeout, the routine first loads 184 the interval register with the paced interval parameters. In the triggered mode, this determination is bypassed since timer T5 determines the pacing interval, as hereinabove set forth. The various wakeup masks for sensed event LA, timer T2 and timer T3 are disabled 250. It should be noted that timer T1 remains enabled in a wakeup condition, if T1 has not timed out. The X register is loaded 254 with the selected pulse width, the selected refractory period is loaded 256 into timer T1, tachycardia counter B3 is reset 258 to "8," and the PACE subroutine is called 260 to generate the output pulse.

When the PACE routine is complete, the system then performs various routines prior to going to sleep in preparation for a next series of timing sequences. First, QT flag B1 and noise counter B2 are reset 262 to "0." This also occurs following the sensing of a tachycardiac pulse (see FIG. 9) which does not initiate the tachycardia arrest routine.

Figure 12:
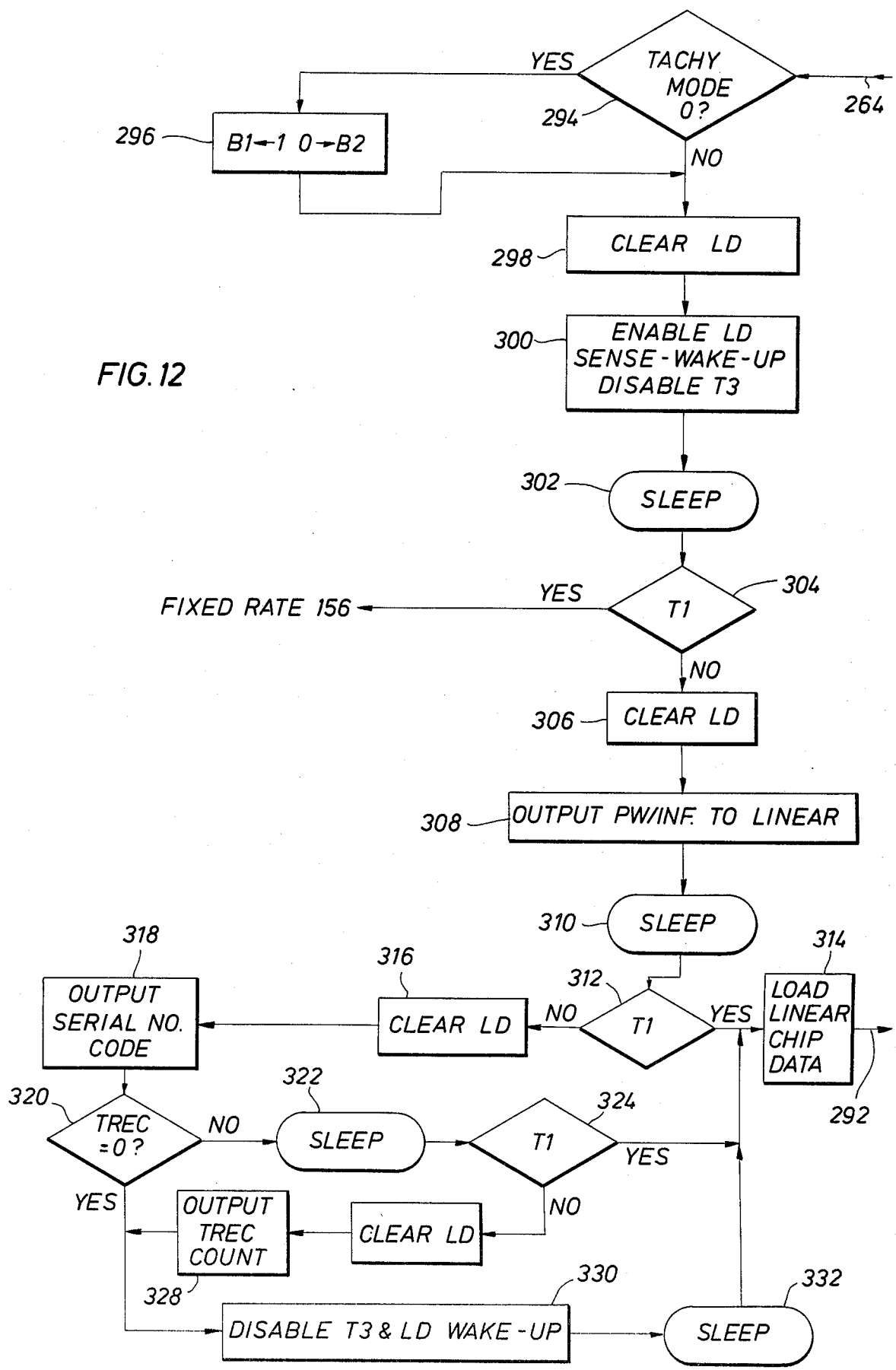
FIG. 12 is a flow diagram for loading pulse parameters and for data telemetry.

A magnetic reed switch may be provided to obtain a program variation from an external signal. Reed switch input IV 3 is interrogated 264. If the reed switch is activated, the operating sequence depicted in FIG. 12 is carried out, as hereinafter discussed.

If the reed switch is not activated, the routine then interrogates 266 whether the various operating parameters are indicated to be temporary parameters. If temporary conditions have been provided, then the temporary indicator register is decremented 274 and the final resetting routine depicted in FIG. 11 is performed. If temporary parameters have not been selected, the routine interrogates 268 counter B4 to determine whether new operating parameters have been provided for pacer 10 (see FIG. 1). If new operating parameters have been provided, B4 is cleared 270 and the new operating parameters are transferred 272 to pacer 10 (see FIG. 1). If no new values have been provided, the loading step 272 is bypassed and the final operating sequence depicted in FIG. 11 is performed.

Referring now to FIG. 11, there is depicted the operating sequence for returning the processor to the initial operating routine depicted in FIG. 7. Where temporary values have been provided, the temporary condition counter is interrogated 276 to determine whether the desired number of temporary pulses have been provided. If the temporary conditions persist, counters B1 and B2 are set 290 to "0" and the processor goes to sleep 292 setting all the timers and wakeup conditions for fixed rate operation 156.

If the temporary condition no longer exists, then the refractory period setting 278, timer T1 setting 280, paced interval setting 282, and interval setting 284 are all reset to the conditions existing prior to the temporary conditions.

Thus, whenever the normal pulsing parameters are to be repeated or when the system is restored to the previous operating parameters, the system then interrogates 286 the mode register. If the mode register indicates "0," the system returns to fixed rate pacing. If the mode register is not "0," the system returns to synchronous pacing, either ventricular inhibited or ventricular triggered. The processor goes to sleep 288 setting the parameters for synchronous mode operation 148 (FIG. 7).

Referring now to FIG. 12, there is depicted an operating sequence activated by reed switch interrogation 264 (see FIG. 10). If the patient has a history of tachycardia, the programmer can provide an indication of this condition and this indicator is interrogated 294 prior to data telemetry. If the patient is not sensitive, B1 is set to a "1" count, wherein the system indicates the QT interval is completed, thus allowing programmed rate pacing during subsequent pacing. If the patient is sensitive, then the routine proceeds directly with B1 set to "0." This condition is interpreted as a noise condition during subsequent flag interrogation and pacing will be initiated at the noise rate, hereinabove discussed. An available wakeup latch LD is cleared 298 and then enabled 300 as a wakeup condition while disabling noise wakeup latch T3.

Timer T1 is interrogated 304 to determine whether the refractory interval is persisting. If timer T1 has timed out, the operation reverts to the fixed rate routine 156 (see FIG. 1). If the system is still in the refractory interval, latch LD is again cleared 298 and the processor transfers operating data to pacer 10 (see FIG. 1) for transmittal via telemetry to the external programmer. Timer T1 is again interrogated 312. If the refractory period has now expired, the operating parameters for pacer 10 are loaded 314 back into the pacer to replace the parameters serially telemetried from pacer 10. Fixed rate operation 156 is then resumed.

If the pacer is still in the refractory period, latch LD is again cleared 316 and other information is telemetered from the system. Typically, the pacer serial number is output 318. If provided, the tachycardia record register is interrogated 320 to determine whether any tachycardiac events have occurred. If there have been tachycardiac events, timer T1 is interrogated 324 and if the refractory period persists, latch LD is cleared 326 and the tachycardia record is output 328. When no tachycardias have occurred or after outputting the contents of the tachycardia register, the wakeup register corresponding to latch LD and timer T3 is disabled 330 and the processor sleeps 332 until waked up by timer T1. It should be noted that the occurrence of a wake up event indicated by timer T1 causes the pacer 10 operating parameters to be transferred from processor 12 to pacer 10 and the routine established at fixed rate pacing 156 until a new operating mode is selected.

It is apparent that the operating sequence hereinabove described provides for controlling the operation of a cardiac pacer using a microprocessor and provides a system which is completely implantable. The system operates only when necessary to process information related to discrete events and sleeps during the interim, thereby consuming only the small amount of energy compatible with implanted operation. It will also be appreciated that the operation as hereinabove described is responsive to a variety of physiological needs and a variety of operating environments such that reliable cardiac pacing operations are maintained.

It is also apparent that the microprocessor apparatus for activating internal logic components only in response to selected physiological events or at selected sample, or timeout, intervals and for operating counters at a plurality of count rates in order to minimize power consumption has wide applicability for implantable devices useful in providing body function assistance. Likewise, the provision of a true reprogrammable implantable device provides a degree of non-invasive versatility not heretofore available.

It will be also appreciated that numerous variations and modifications may obviously be made in the structure herein described and shown in the accompanying drawings is illustrative only and is not intended to limit the scope of the invention.

What is claimed is:

1. A method of reducing the power consumption of a microprocessor controlled system comprising the steps of:
    (a) storing a wakeup parameter;
    (b) operating the microprocessor in a sleep state wherein no processing activity or a predetermined sleep processing activity occurs;
    (c) generating event signals upon the occurrence of corresponding predetermined events; and
    (d) operating the microprocessor with a processing activity increased with respect to the activity occurring during said sleep state, in response to a generated event signal which corresponds to the stored wakeup parameter.

2. The method of claim 1 wherein step (a) includes the step of selecting at least one wakeup parameter from a predetermined set of wakeup parameters.

3. The method of claim 2 wherein step (c) includes the step of receiving a time-out signal from at least one counter and generating the event signal therefrom.

4. The method of claim 3 wherein step (c) further includes the step of receiving a plurality of time-out signals from counters which count at different rates functionally related to a heart refractory period, a normal heartbeat rate, and a tachycardiac heartbeat rate and generating event signals corresponding thereto.

5. A method according to claim 4, further including the steps of:
    correlating said occurrence of an external event signal with the occurrence of said at least one timeout signal, and
    deriving from said correlation signal an output signal indicative of a physiological condition associated with said external event signal.

6. The method of claim 2 wherein step (c) includes the step of sensing cardiac activity and generating the event signal in response thereto.

7. The method of claim 2 including the step of selecting the wakeup parameter as a function of the generated event signal.

8. A method according to claim 7, including the steps of:
    timing a selectable refractory interval functionally related to the refractory interval of a heart,
    thereafter timing a selectable quiet interval while detecting the occurrence of external events, resetting said quiet interval whenever an external event has occurred within said quiet interval, said quiet interval being selected to correlate with "T" wave generation following a cardiac contraction.

9. A method according to claim 8, including the steps of:
timing a tachycardia interval following said refractory interval while detecting the occurrence of sensed events,
deriving a tachycardiac signal indicative of a sensed event occurring after timeout of said quiet interval and during said tachycardia interval; and
generating a tachycardia arrest routine after a selectable number of sequential tachycardiac signals are obtained.

10. A method according to claim 8 or 9, including the steps of:
timing a noise interval following said refractory interval while detecting the occurrence of sensed events,
generating an output pulse control routine when said noise interval times out and a selectable number of sensed events has been detected.

11. A method according to claim 10, including the steps of:
disabling wakeup events other than noise interval timeout during said noise interval once said selectable number of sensed events has been detected.

12. The method of claim 1 or 2 wherein steps (a) through (d) are performed repeatedly in a sequence effective to maintain an average current consumption of less than 50 microamperes for the microprocessor controlled system.

13. A method according to claim 12, wherein said average current consumption is about 10 microamperes.

14. The method of claim 1 wherein:
step (a) includes the step of storing the wakeup parameter in a wakeup mask register; and
step (d) includes the step of applying the generated event signal to the wakeup mask register.

15. A microprocessor controlled system comprising:
a microprocessor with means for operating to perform logic functions;
means for storing a mask signal representing a wakeup parameter;
means for suspending the execution of logic functions by the microprocessor;
means for detecting at least one predefined wakeup condition; and
means for enabling the microprocessor to execute logic functions in response to the detection of a wakeup condition which corresponds to said stored mask signal.

16. The microprocessor control system of claim 15 wherein said means for detecting comprises:
circuit means for generating an event signal indicating the occurrence of a predetermined event; and
timer means for generating a time-out signal indicating the occurrence of a timed interval event.

17. The microprocessor control system of claim 16 wherein the timer means includes means for generating timing pulses at a plurality of frequencies in order to produce time-out signals with selected degrees of accuracy.

18. The microprocessor control system of claim 15 including means for deriving the mask signal as a function of the wakeup signal.

19. A body function assistance device having a control system, including a microprocessor with internal logic components, for generating control signals to control a bodily function and for receiving and responding to signals generated by the body, the improvement comprising:
sleep state inducing means for deactivating the internal logic components of the microprocessor to cause the microprocessor to enter a sleep state;
wakeup condition indicating means for holding information indicative of conditions under which the microprocessor's internal logic components are to be activated;
event signal generating means for generating an event signal indicating the occurrence of a predetermined event; and
sleep state terminating means for activating the internal logic components of the microprocessor when the signal generated by the event signal generating means corresponds to the condition held in the wakeup condition indicating means.

20. The apparatus of claim 19 wherein the body function assistance device comprises an implantable heart pacer including:
heart stimulating means for pacing the heart;
heart sensing means for detecting electrical signals of the heart;
means for generating a wakeup condition signal as a function of the event signal; and
means for storing the wakeup condition signal in the wakeup condition indicating means.

21. The apparatus of claim 20 including timing means for generating a time-out signal after a predetermined time interval;
said event signal generating means having means for generating an event signal in response to the time-out signal and in response to signals detected by the heart sensing means; and
said wakeup condition signal generating means having means for selecting at least one wakeup condition from among a predetermined set of wakeup conditions, each condition in the set corresponding to one signal produced by the event signal generating means.

22. A method of reducing the power consumption of a microprocessor control system comprising the steps of:
(a) storing a wakeup parameter;
(b) putting the microprocessor in a sleep state wherein no processing activity occurs;
(c) generating an event signal upon the occurrence of a predetermined event; and
(d) resuming processing activity when the generated event signal corresponds to the stored wakeup parameter.

23. The method of claim 22 wherein the microprocessor control system controls the operation of a heart pacer and includes the steps of:
sensing cardiac activity;
receiving a time-out signal from a counter;
generating an event signal in response to the sensed cardiac activity and the time-out signal;
executing a predetermined sequence of steps in response to an event signal which corresponds to the stored wakeup parameter;
generating stimulating signals to stimulate the heart; and selecting at least one wakeup parameter from a predetermined set of wakeup parameters as a function of the generated event signal.

24. A microprocessor controlled system comprising:

a microprocessor with means for operating to perform logic functions;

means for selectively suspending the execution of logic functions by the microprocessor;

means for detecting at least one predefined activation condition; and means for starting the execution of logic functions by the microprocessor in response to the detection of said predefined activation condition.

* * * * *

UNITED STATES PATENT AND TRADEMARK OFFICE
CERTIFICATE OF CORRECTION

PATENT NO. : 4,404,972　　　　　　　　　　　Page 1 of 2 pages

DATED : September 20, 1983

INVENTOR(S) : Pat L. Gordon, Richard V. Calfee, and Jay Miner

It is certified that error appears in the above-identified patent and that said Letters Patent is hereby corrected as shown below:

On the first page, under "U.S. Patent Documents", after "Alley" insert --III--;

in the specification:

column 1, line 65, delete "complimentary" and insert --complementary--;

column 10, line 36, delete "approproate" and insert --appropriate--;

column 12, line 9, delete "agains" and insert --again--;

column 12, line 20, delete "sense" and insert --sensed--;

column 15, line 53, delete "When" and insert --Where--;

column 15, line 57, delete "waked up" and insert --awakened--;

UNITED STATES PATENT AND TRADEMARK OFFICE
CERTIFICATE OF CORRECTION

PATENT NO. : 4,404,972
DATED : September 20, 1983
INVENTOR(S) : Pat L. Gordon, Richard V. Calfee, and Jay Miner It is certified that error appears in the above-identified patent and that said Letters Patent is hereby corrected as shown below:

in Claim 11, line 2, delete "steps" and insert --step--.

Signed and Sealed this

Eleventh Day of September 1984

[SEAL]

Attest:

GERALD J. MOSSINGHOFF

Attesting Officer     Commissioner of Patents and Trademarks

REEXAMINATION CERTIFICATE (4111th)

United States Patent [19]
Gordon et al.

[11] B1 4,404,972
[45] Certificate Issued Jul. 11, 2000

[54] IMPLANTABLE DEVICE WITH MICROPROCESSOR CONTROL

[75] Inventors: Pat L. Gordon, West Columbia; Richard V. Calfee, Houston, both of Tex.; Jay Miner, Sunnyvale, Calif.

[73] Assignee: Intermedics, Inc., Freeport, Tex.

Reexamination Request:
No. 90/004,697, Jul. 11, 1997

Reexamination Certificate for:
Patent No.: 4,404,972
Issued: Sep. 20, 1983
Appl. No.: 06/264,670
Filed: May 18, 1981

[51] Int. Cl.$^7$ .................................................. A61N 1/36
[52] U.S. Cl. .................................................. 607/16
[58] Field of Search .............. 607/9, 16; 364/140.01, 364/141

[56] References Cited

U.S. PATENT DOCUMENTS

| | | | |
|---|---|---|---|
| 3,286,239 | 11/1966 | Thompson et al. | 340/172.5 |
| 3,453,601 | 7/1969 | Bogert et al. | 340/172.5 |
| 3,535,560 | 10/1970 | Cliff | 307/296 |
| 3,557,796 | 1/1971 | Keller, Jr. et al. | 128/419 |
| 3,736,569 | 5/1973 | Bouricius et al. | 340/172.5 |
| 3,820,079 | 6/1974 | Bergh et al. | 340/172 |
| 3,921,642 | 11/1975 | Preston et al. | 128/419 |
| 3,941,989 | 3/1976 | McLaughlin et al. | 235/156 |
| 3,955,355 | 5/1976 | Luce | 58/50 |
| 3,970,998 | 7/1976 | Weisbecker | 340/172 |
| 4,003,028 | 1/1977 | Bennett et al. | 340/172 |
| 4,004,283 | 1/1977 | Bennett et al. | 340/172 |
| 4,010,448 | 3/1977 | Bennett et al. | 340/172 |
| 4,032,896 | 6/1977 | Bennett et al. | 364/200 |
| 4,037,204 | 7/1977 | Bennett et al. | 364/200 |
| 4,038,641 | 7/1977 | Bouknecht et al. | 364/900 |
| 4,079,251 | 3/1978 | Osann, Jr. | 250/231 |
| 4,080,659 | 3/1978 | Francini | 364/715 |
| 4,086,627 | 4/1978 | Bennett et al. | 364/200 |

(List continued on next page.)

FOREIGN PATENT DOCUMENTS

| | | |
|---|---|---|
| 77-28936 | 9/1977 | France . |
| 26-31-840 A1 | 6/1976 | Germany . |
| 1524795 | 9/1978 | Germany . |
| 1542814 | 3/1979 | Germany . |
| 55-13443 | 5/1978 | Japan . |
| 53-68051 | 6/1978 | Japan . |
| 53-116750 | 10/1978 | Japan . |
| 58-72266 | 10/1981 | Japan . |
| 2002156 | 2/1979 | United Kingdom . |
| 2006015 | 5/1979 | United Kingdom . |
| 2026870 | 2/1980 | United Kingdom . |

OTHER PUBLICATIONS

RCA Solid State "COS/MOS Integrated Circuits" (CPI 1508349–369) (no date).

Smith, P. et al., "C–MOS Microprocessor Wakes Itself Up," Electronics, Sep. 25, 1980, pp. 123–126.

Webster, J., "An Intelligent Monitor For Ambulatory ECGS," Biomedical Sciences Instrumentation, vol. 14, Apr. 17–18, 1978.

(List continued on next page.)

Primary Examiner—Jeffrey R. Jastrzab

[57] ABSTRACT

An improved body function assistance device is provided wherein a microprocessor controls the response of the device to various external physiological events and internal timer events. The microprocessor is adapted for use with the limited energy supply available from a battery by activating internal logic components of the processor only in response to selected events and to perform an operating routine corresponding to the "wakeup" event. At the end of the operating routine, a new set of wakeup events is selected and the internal logic components are deactivated. A further reduction in the average operating current is obtained by providing a plurality of counting rates to minimize the number of state changes during counting cycles. The microprocessor may be provided with a fixed operating routine or may be provided with the capability of actually introducing program changes in the implanted device.

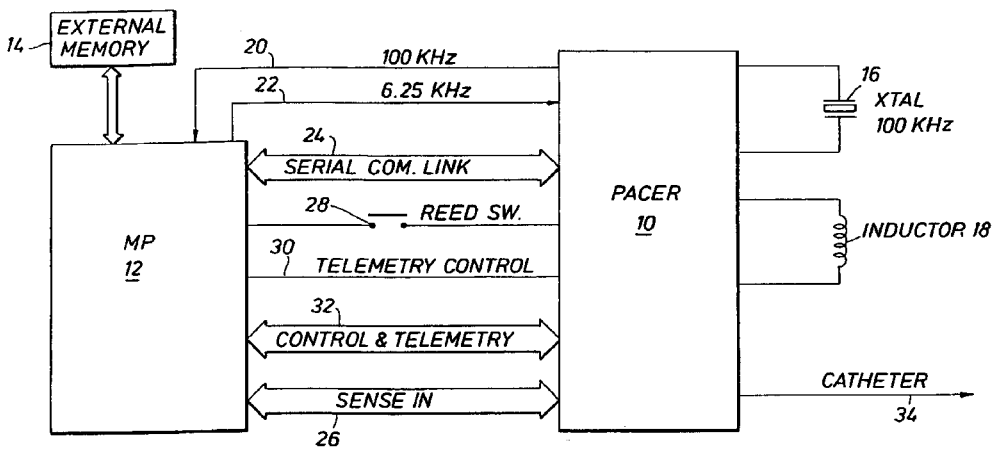

U.S. PATENT DOCUMENTS

| | | | |
|---|---|---|---|
| 4,087,854 | 5/1978 | Kinoshita et al. | 364/200 |
| 4,090,236 | 5/1978 | Bennett et al. | 364/200 |
| 4,109,315 | 8/1978 | Pan | 364/705 |
| 4,112,490 | 9/1978 | Pohlman et al. | 364/200 |
| 4,132,233 | 1/1979 | Hartlaub | 128/419 |
| 4,137,563 | 1/1979 | Tsunoda | 364/200 |
| 4,143,417 | 3/1979 | Wald et al. | 364/900 |
| 4,146,029 | 3/1979 | Ellinwood, Jr. | 128/200 |
| 4,149,257 | 4/1979 | Nakagiri et al. | 364/705 |
| 4,158,230 | 6/1979 | Washizuka et al. | 364/708 |
| 4,158,285 | 6/1979 | Heinsen et al. | 58/23 |
| 4,159,516 | 6/1979 | Henrion et al. | 364/200 |
| 4,161,782 | 7/1979 | McCracken | 364/571 |
| 4,161,787 | 7/1979 | Groves et al. | 364/900 |
| 4,164,944 | 8/1979 | Alley, III et al. | 128/419 |
| 4,171,539 | 10/1979 | Tawfik et al. | 364/900 |
| 4,181,934 | 1/1980 | Marenin | 364/200 |
| 4,203,153 | 5/1980 | Boyd | 364/200 |
| 4,204,249 | 5/1980 | Dye et al. | 364/200 |
| 4,218,876 | 8/1980 | Hashimoto et al. | 368/10 |
| 4,222,385 | 9/1980 | Backhouse | 128/419 |
| 4,240,150 | 12/1980 | Ebihara et al. | 364/705 |
| 4,254,475 | 3/1981 | Cooney et al. | 364/900 |
| 4,279,020 | 7/1981 | Christian et al. | 364/900 |
| 4,287,559 | 9/1981 | Easley et al. | 364/200 |
| 4,287,560 | 9/1981 | Forbes et al. | 364/200 |
| 4,290,429 | 9/1981 | Blaser | 128/419 |
| 4,300,195 | 11/1981 | Raghunathan | 364/200 |
| 4,304,237 | 12/1981 | Mensink | 128/419 |
| 4,308,593 | 12/1981 | Young et al. | 365/15 |
| 4,308,866 | 1/1982 | Jelliffe et al. | 128/214 |
| 4,365,290 | 12/1982 | Nelms et al. | 364/200 |
| 4,376,973 | 3/1983 | Chivers | 364/200 |
| 4,381,552 | 4/1983 | Nocilini et al. | 364/900 |
| 4,388,927 | 6/1983 | Schober | 128/419 |
| 4,407,288 | 10/1983 | Langer et al. | 128/419 |
| 4,424,812 | 1/1984 | Lesnick | 128/419 |
| 4,435,761 | 3/1984 | Kimoto | 364/200 |
| 4,479,191 | 10/1984 | Nojima et al. | 364/707 |
| 4,545,030 | 10/1985 | Kitchin | 364/900 |
| 4,590,943 | 5/1986 | Paull et al. | 128/419 |
| 4,748,559 | 5/1988 | Smith et al. | 364/200 |
| 4,758,945 | 7/1988 | Remedi | 364/200 |
| 4,958,632 | 9/1990 | Duggan | 128/419 |

OTHER PUBLICATIONS

Tompkins, W., "A Portable Microcomputer–Based System For Biomedical Applications," Biomedical Sciences Instrumentation, vol. 14, 1978, pp. 61–66.

Osborne & Associates, "The MC6809 Microprocessor," An Introduction To Microcomputers Volume 2—Some Real Microprocessors (Chapter 9), 1978–79, pp. 9–175 to 9–211 and 9–D1 to 9–D39.

Osborne & Associates, "The National Semiconductor COP400 Series Single–Chip Microcomputers", An Introduction To Microcomputers Volume 2—Some Real Microprocessors (Chapter 1), 1978–79, pp. 1–22 to 1–49.

Berkman, J. et al., "Biomedical Microprocessor with Analog I/O," 1981 IEEE International Solid–State Circuits Conference, Feb. 1981, pp. 168–169.

User Manual for the CDP1802 COSMAC Microprocessor, RCA/Solid State Division, Copyright 1976 by RCA Corporation.

Osborne & Associates, "The National Semiconductor SC/MP," An Introduction To Microcomputers Volume 2—Some Real Microprocessors (Chapter 3), 1978–79, pp. 3–1 to 3–33 and 3–D1 to 3–D11.

Osborne & Associates, "1M6100 Microcomputer Devices," An Introduction To Microcomputers Volume 2—Some Real Microprocessors (Chapter 13), 1978–79, pp. 13–1 to 13–88 and 13–D1 to 13–D6.

Hersberger, P., "Proges Dans La Conception Et La Fabrication Des Circuits Integres A Esa," CIC Geneve, Conference No. E1.5, 1979, pp. 265–269.

Burlew, L. et al., "Copy Finisher," 16731, Research Disclosure, Mar. 1978, pp. 61–67.

Martin, J., "The Use of ROM's and RAM's In A Wrist–Watch," CIC Geneve, Conference No. E2.3, 1979, pp. 285–291.

"Digital Wristwatch Contains A Scientific Calculator," Electronic Design, No. 5, Mar. 1, 1977, p. 17.

"Microprocessor Set Uses C–MOS," Electronics, Mar. 31, 1977, p. 130.

"HP Wristwatch—First With Timely Calculations," Electronic Design, No. 13, Jun. 21, 1977, p. 17.

"Watch Chip Is Programmable," Electronics, Apr. 29, 1976, p. 147.

"National Expands Processor Line," Electronics, May 27, 1976, pp. 146, 148.

"Programmable Chip Eyed For Watches," Electronics, Feb. 5, 1976, pp. 32, 34.

Kurita, H. et al., "Multifunction Digital Quartz Watches," CIC Geneve, Conference No. C2.2, 1979, pp. 301–307.

Peppiette, G., "Memory Architecture And The Influence Of The Microprocessor," Microelectronics and Reliability, vol. 15, 1976, pp. 307–313.

Bishop, R., "L.S.I. CMOS Applications," Microelectronics and Reliability, vol. 16, 1977, pp. 461–475.

Motorola's M6805 HMOS M146805 CMOS Family, Microcomputer/Microprocessor User's Manual, 1980, pp. 44–46, 80–82, 86, 101–103, 124, 211 and 219.

Ripart, A. et al., "Clinical Value Of A Microcomputer In An Implantable Pacemaker," Applications of Computers in Cardiology, 1984, pp. 143–146.

Elmquist, H., "Chapter Four—Cardiac Pacemaker Intelligence vs. Power Consumption," The Third Decade of Cardiac Pacing: Advances in Technology and Clinical Applications, 1982, pp. 445–450.

Zissos, D. et al., "Wait/Go Microprocessor Systems," Nov. 11–18, 1997, pp. 112–121.

Grundy, K. et al., "Speed—Energy Considerations Of Microprocessors And APU's For Tactical Missile Applications," American Institute of Aeronautics and Astronautics, Inc., 1979, pp. 162–168.

Bliss, C., "Stopping The 8080," Electronics Industry, Nov. 1976, pp. 19–21.

Motorola's M6800 Microprocessor Application Manual, 1975, pp. 1–8, 4–13 and 4–42 to 4–45.

RCA's User Manual For The CDP1802 COSMAC Microprocessor, 1976, pp. 7–9 and 70–72.

Martin, J. et al., "A Review Of Microprogrammed Wrist Watches," From Electronics to Microelectronics, Fourth European Conference on Electronics—EUROCON '80, Stuttgart, Germany, Mar. 24–28, 1980, pp. 626–631.

Listing of Portable Computers, BYTE Publications, Inc., Sep. 1983, pp. 36–45.

Waldvogel, A., "A One Chip Microcomputer For Watch Applications," ESSCIRC '80, Grenoble, Sep. 1980, pp. 268–270.

Korn, G., "Chapter 4—Interfacing Microprocessors And Minicomputers With Real–World Devices," Microprocessors And Small Digital Computer Systems for Engineers And Scientists, 1973, pp. 140–151.

Tocci, R. et al., "Device–Initiated I/O Transfer–Interrupts," Microprocessors and Microcomputers: Hardware and Software, 1979, pp. 172–182.

Rockwell International Corporation, "PPS–4/1 Microcomputer—MM78LS System," Rockwell's Parallel Processing System PPS Data Sheet, Jun. 1982, pp. 2–6.

Osborne & Associates, "4–Bit Microprocessors," An Introduction To Microcomputers Volume 2—Some Real Microprocessors (Chapter 1), 1978–1979, pp. 1–1 to 1–21.

Texas Instruments TMS 1000 CMOS Family Data Manual, Dec. 1978.

Encyclopedia of Computer Science (Van Nostrand), 1976, pp. 733–736.

Mostek 1979 Microcomputer Data Book, Jun. 1979.

Intel Component Data Catalog.

Intel 8086 Family User's Manual, Oct. 1979.

Tamir, D., "Design Of A 16K Electrically Programmable Microprocessor Peripheral Chip," The Tenth Convention of Electrical and Electronics Engineers In Israel, Tel–Aviv, Oct. 10–13, 1977, pp. 126–128.

Johnson, E., "Design Of A 'Hybrid' Microprocessor Development System," Micro 77 Computer Conference Record, Lincoln Plaza Forum, Oklahoma City, Apr. 6–8, 1977 pp. 13–17.

Sansen, W. et al., "A Microprocessor Compatible Multi–Channel Interface System For Sensor Signal Processing," IEEE, 1985, pp. 275–278.

Dollhoff, T., "Circuit Allows Program–Halt And Single–Instruction Mode On $\mu$P," Electronic Design, No. 2, Jan. 18, 1977, p. 94.

Hoff, W., "Optimum Design Techniques For Micropower Circuitry," IEEE Journal of Solid–State Circuits, vol. SC–7, No. 2, Apr. 1972, pp. 168–170.

Tangri, N., "Choosing Optimal Microprocessor Clock Frequency Minimizes Power Consumption," Computer Design, vol. 20, No. 8, Aug. 1981, pp. 138–144.

Gascón, D. et al., "Cardiac Stimulator Controlled By A Microprocessor," Applications of Computers in Cardiology, 1984, pp. 147–151.

Zaks, R., "Programming the Z80", Sybex Computer Books, 3rd Revised Edition, Copyright 1979, 1982, pp 185, pp 257.

Zaks, R. et al., "Microprocessor Interfacing Techniques", Sybex, Copyright 1977, 1978, 1979, pp 74–87.

Moore, A.W. et al., "Microprocessor Applications Manual", Motorola Semiconductor Products, Inc., Copyright 1975, pp 1–1 and 1–2.

Hellerman, H., "Digital Computer System Principles", Copyright 1967, pp 350–355.

Motorola MC6800 Materials (untitled), (undated), pp 1–19, 1–33, 1–37, 1–38, 3–2 to 3–11.

Winter, K. et al., "All–CMOS Components Build a $\mu$C System That Checks Power Loss, Eases Regulation", Electronic Design No. 8, Apr. 12, 1980, pp 141–146.

Donoghue, B., "C–MOS Read–Only Memory Mates With a Host of Processors", Electronics, Sep. 25, 1980, pp 127–129.

Applied Ideas (author unknown), "Power–On Reset/Run Circuits for the CDP 1802 $\mu$P", Electronic Engineering, Sep., 1979, pp 25.

Sub–Systems and Peripherals (author unknown), "Microcomputer System", Electronic Engineering, Mid–Sep., 1979, pp 47.

Dozier, H.W., et al., "RAM–ROM Single–Chip Miocrocomputer Expands Its Memory", Electronics, May 11, 1978, pp 105–110.

Zilog (author unknown), "Zilog Fortran User Guide", Copyright 1978, pp 1–17.

Zilog Z8001 CPU and Z8002 CPU Product Specification, Preliminary, Mar., 1979, pp 1–25.

Zilog Z8000 Family, Technical Overview, Aug., 1979, (unnumbered pages).

Zilog "The Z8000 Family of Microcomputer Components", Copyright 1978, (no page numbers).

Stevenson, D., "An Introduction to the Z8010 MMU Memory Management Unit, Tutorial Information", Oct., 1979, pp 2–20.

Leventhal, L., "Z80 Assembly Language Programming", Copyright 1979.

Zilog "Z80–Assembly Language Programming Manual", Copyright 1977, 1978, pp 1–296.

Zilog "Microprocessor Applications Reference Book", vol. 1, Jul., 1981, pp 1–1 to 6–78.

Zilog "Fortran IV Language Manual", Copyright 1977, 1978, pp 1–1 to E–2.

Zilog "Z8000 CPU, Instruction Set, Preliminary", Feb., 1979, selected pages, including unnumbered pages.

Zilog "Z80–RIO Operating System User's Manual", date unknown.

Zaks, R., "Programming the Z80", Sybex, Copyright 1979, pp 1–624.

Hordeski, M.F., "Microprocessor Cookbook", Copyright 1979, pp 1–E64.

Chandor, A. et al., "The Penguin Dictionary of Computers", Copyright 1979, 1977, pp 1–440.

Mateosian, R., Programming the Z8000, Sybex, Copyright 1980, pp 1–298.

Leventhal, L., "Introduction to Microprocessors: Software, Hardware, Programming", Copyright 1978, pp. 1–X24.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–24 is confirmed.

* * * * *